(12) United States Patent
Fukuhara et al.

(10) Patent No.: US 10,244,937 B2
(45) Date of Patent: Apr. 2, 2019

(54) IMAGE PROCESSING APPARATUS AND IMAGE PROCESSING METHOD

(71) Applicant: CANON KABUSHIKI KAISHA, Tokyo (JP)

(72) Inventors: Makoto Fukuhara, Yokohama (JP); Makoto Sato, Tokyo (JP); Yoshihiko Iwase, Yokohama (JP); Nobuhiro Tomatsu, Yokohama (JP); Tomoyuki Makihira, Tokyo (JP); Kazuhide Miyata, Yokohama (JP); Hiroyuki Shinbata, Tama (JP); Ritsuya Tomita, Yokohama (JP); Daisuke Kibe, Kawaguchi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/909,064

(22) PCT Filed: Jul. 24, 2014

(86) PCT No.: PCT/JP2014/070146
§ 371 (c)(1),
(2) Date: Jan. 29, 2016

(87) PCT Pub. No.: WO2015/016290
PCT Pub. Date: Feb. 5, 2015

(65) Prior Publication Data
US 2016/0198939 A1    Jul. 14, 2016

(30) Foreign Application Priority Data
Jul. 31, 2013    (JP) .................................. 2013-159177

(51) Int. Cl.
*A61B 3/00* (2006.01)
*A61B 3/113* (2006.01)
(Continued)

(52) U.S. Cl.
CPC .......... *A61B 3/0025* (2013.01); *A61B 3/0041* (2013.01); *A61B 3/102* (2013.01);
(Continued)

(58) Field of Classification Search
CPC ..... A61B 3/0025; A61B 3/102; A61B 3/0041; A61B 3/14; A61B 3/1225; A61B 3/1005; A61B 3/113
(Continued)

(56) References Cited

U.S. PATENT DOCUMENTS

2002/0091323 A1    7/2002    Dreher
2009/0268162 A1   10/2009    Stetson
(Continued)

FOREIGN PATENT DOCUMENTS

CN    102985785 A    3/2013
CN    103025229 A    4/2013
(Continued)

OTHER PUBLICATIONS

Erich Gotzinger, High Speed Spectral Domain Polarization Sensitive Optical Coherence Tomography of the Human Retina, Optics Express 10217, Dec. 12, 2005, vol. 13, No. 25.

*Primary Examiner* — Jack Dinh
(74) *Attorney, Agent, or Firm* — Canon U.S.A., Inc. IP Division

(57) ABSTRACT

To provide pathological support for users to effectively perform follow up on diseases, using polarization information obtained from polarization-sensitive tomographic images.
An image processing apparatus includes a positioning unit configured to position multiple polarization-sensitive tomographic images corresponding to multiple tomographic luminance images, based on the plurality of tomographic luminance images obtained by photographing an object at
(Continued)

different times; and a comparing unit configured to compare the plurality of polarization-sensitive tomographic images which are positioned.

19 Claims, 10 Drawing Sheets

(51) Int. Cl.
   *A61B 3/12*   (2006.01)
   *A61B 3/10*   (2006.01)
   *A61B 3/14*   (2006.01)
   *G06T 7/00*   (2017.01)
   *G06T 7/33*   (2017.01)

(52) U.S. Cl.
   CPC ............ *A61B 3/1005* (2013.01); *A61B 3/113* (2013.01); *A61B 3/1225* (2013.01); *A61B 3/14* (2013.01); *G06T 7/0016* (2013.01); *G06T 7/337* (2017.01); *G06T 2207/10101* (2013.01); *G06T 2207/30041* (2013.01)

(58) Field of Classification Search
   USPC .................................................. 351/206, 246
   See application file for complete search history.

(56) References Cited

U.S. PATENT DOCUMENTS

| 2011/0267340 A1 | 11/2011 | Kraus |
| 2012/0249954 A1 | 10/2012 | Uchida |
| 2013/0188134 A1 | 7/2013 | Iwase |

FOREIGN PATENT DOCUMENTS

| CN | 103211572 A | 7/2013 |
| CN | 103211574 A | 7/2013 |
| JP | 2007252692 A | 10/2007 |
| JP | 2011120656 A | 6/2011 |
| JP | 2011224264 A | 11/2011 |
| JP | 2012016525 A | 1/2012 |
| WO | 2007/058895 A2 | 5/2007 |
| WO | 2009/141769 A1 | 11/2009 |
| WO | 2010/122118 A1 | 10/2010 |

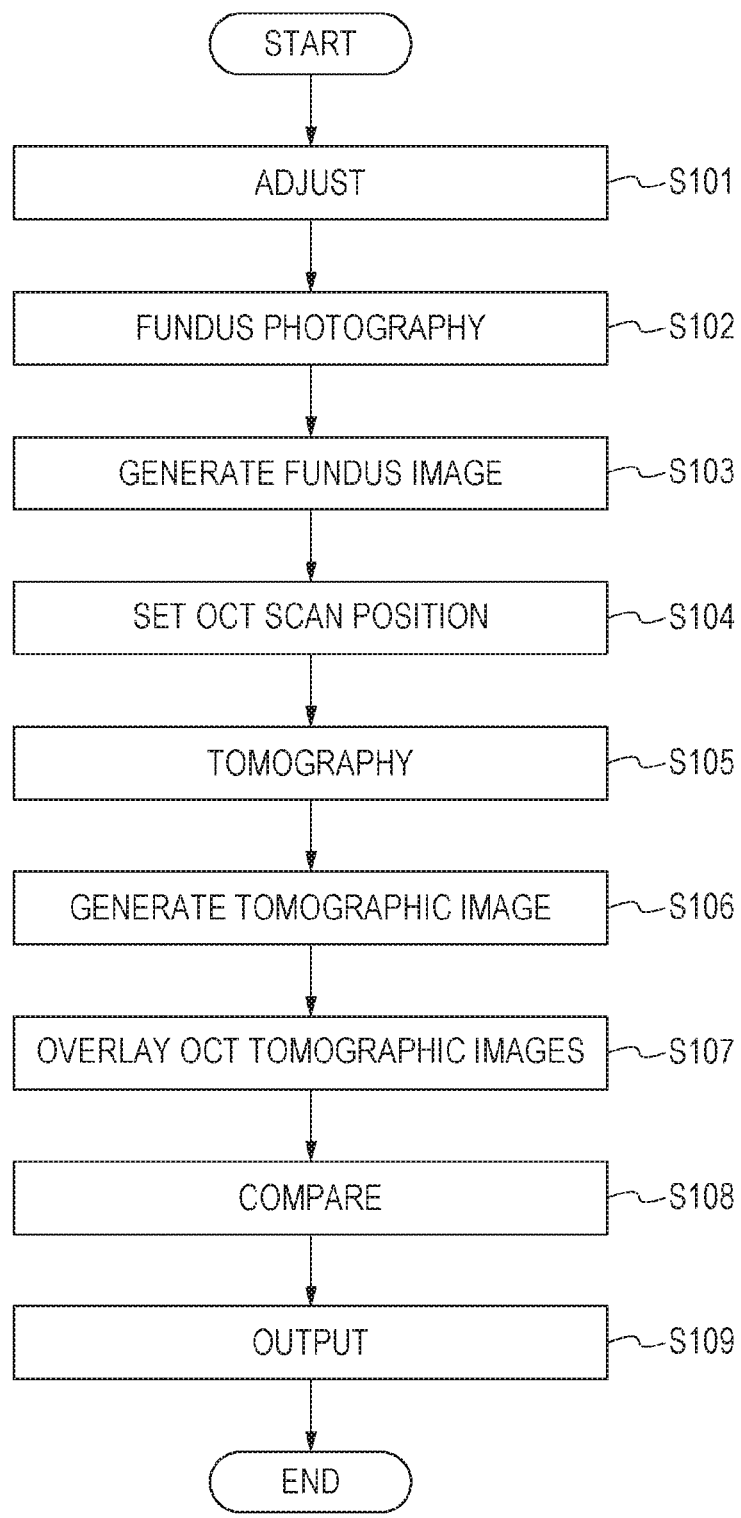

IMAGE PROCESSING APPARATUS AND IMAGE PROCESSING METHOD

TECHNICAL FIELD

The present invention relates to an image processing apparatus which processes images of an object and an image processing method.

BACKGROUND ART

Optical coherence tomography (OCT) using multi-wavelength light-wave interference can obtain tomographic images of specimens (particularly the fundus) at high resolution.

In recent years, the field of ophthalmologic OCT has seen advance in development of polarization sensitive OCT where polarization parameters (retardation and orientation) which are a type of optical properties of fundus tissue are used to perform imaging, in addition to normal OCT where the shape of the fundus tissue is imaged.

A polarization sensitive OCT image can be configured and fundus tissue can be distinguished and segmented (processing where boundaries of layers are calculated from tomographic image data) using polarization parameters in polarization sensitive OCT. Accordingly, tissue which has been difficult to diagnose using luminance information can be distinguished, thereby providing pathological support for diagnosis of glaucoma and so forth.

In polarization sensitive OCT, light, which has been modulated into circularly-polarized light is used as measurement light to observe a specimen, and interference light is split as two orthogonal linearly-polarized lights and detected, thereby generating a polarization sensitive OCT image (see PTL 1).

CITATION LIST

Patent Literature

PTL 1 International Publication No. WO 2010/122118A1

Non Patent Literature

NPL 1 E. Gotzinger et al., Opt. Express 13, 10217, 2005

SUMMARY OF INVENTION

Solution to Problem

An image processing apparatus according to the present invention includes: a tomographic image acquiring unit, configured to acquire a plurality of tomographic luminance images obtained by photographing an object at different times, and a plurality of polarization-sensitive tomographic images corresponding to the plurality of tomographic luminance images; a positioning unit configured to position the acquired plurality of polarization-sensitive tomographic images based on the acquired plurality of tomographic luminance images; and a comparing unit configured to compare the plurality of polarization-sensitive tomographic images which are positioned.

An image processing method according to the present invention includes: a step to acquire a plurality of tomographic luminance images obtained by photographing an object at different times, and a plurality of polarization-sensitive tomographic images corresponding to the plurality of tomographic luminance images; a step to position the acquired plurality of polarization-sensitive tomographic images based on the acquired plurality of tomographic luminance images; and a step to compare the plurality of polarization-sensitive tomographic images which are positioned.

Further features of the present invention will become apparent from the following description of exemplary embodiments with reference to the attached drawings.

BRIEF DESCRIPTION OF DRAWINGS

FIG. 3 is a flowchart illustrating processing according to the first embodiment.

DESCRIPTION OF EMBODIMENTS

Conventionally, there have been no innovations regarding devise or methods to use obtained polarization-sensitive tomographic images to follow up on diseases. It has been found desirable to provide pathological support for users to effectively perform follow up on diseases, using polarization information obtained from polarization-sensitive tomographic images. According to an embodiment, the object is photographed at different times, and the obtained multiple tomographic luminance images are used to perform positioning of multiple polarization-sensitive tomographic images as to the multiple tomographic luminance images. The multiple polarization-sensitive tomographic images which are positioned are compared. This enables providing of pathological support for users to effectively perform follow up on diseases, using polarization information obtained from polarization-sensitive tomographic images.

A photography apparatus according to the present invention can be applied to objects such as eyes, skin, internal organs, and so forth. Examples of photography apparatuses according to the present invention include ophthalmologic apparatuses, endoscopes, and so forth. An ophthalmologic apparatus according to an embodiment will be described in detail with reference to the drawings, as an example of the present invention.

First Embodiment

Overall Configuration of Apparatus

Figure 1:
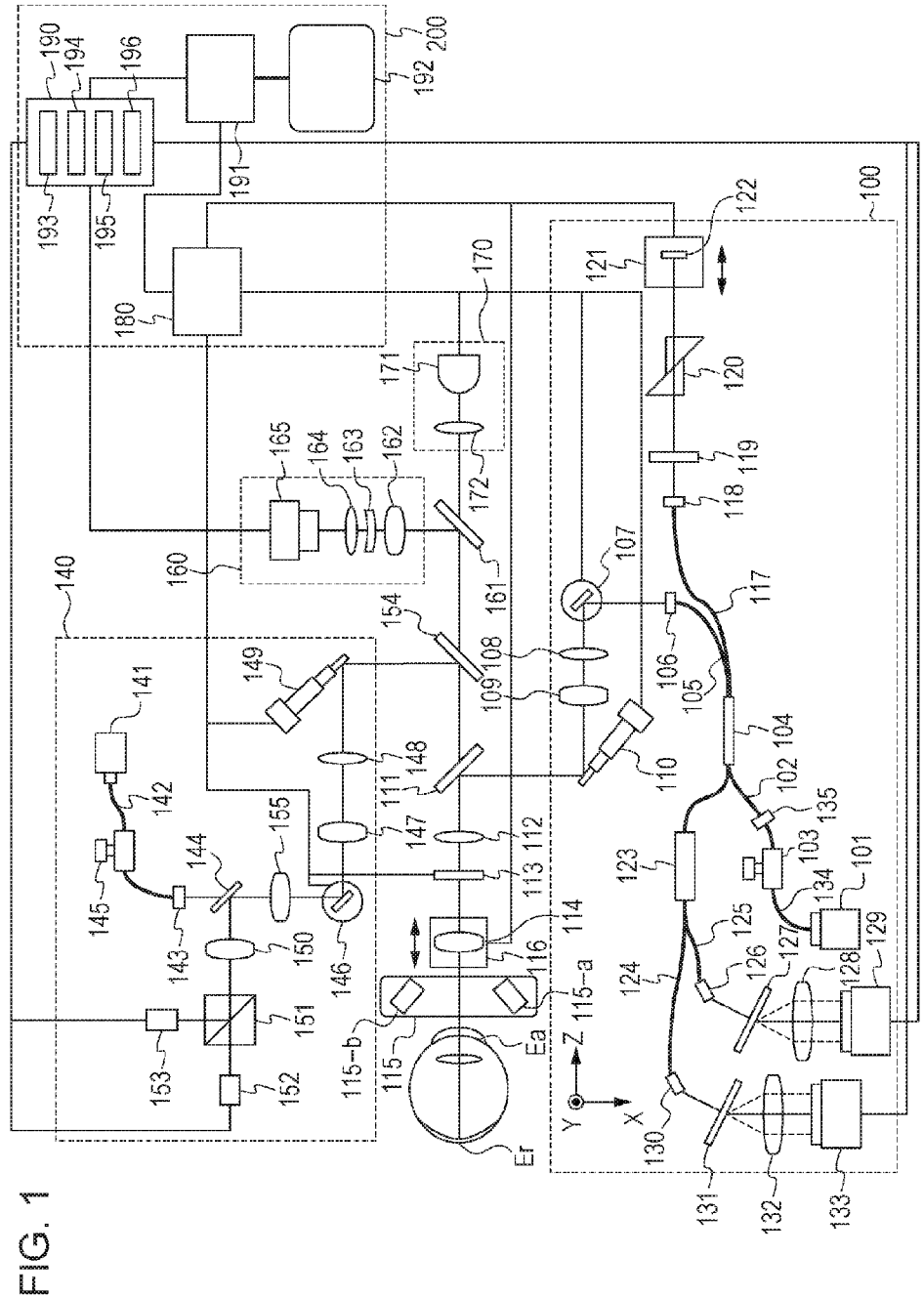
FIG. 1 is a schematic diagram of the overall configuration of an image processing apparatus according to a first embodiment.

FIG. 1 is a schematic diagram illustrating the overall configuration of an ophthalmologic apparatus which is an example of the photography apparatus according to the present embodiment. At least part of a later-described signal processing unit 190 can be deemed to be an "image processing apparatus", in which case the overall "ophthalmologic apparatus" can be deemed to be an "ophthalmologic system", and the overall "photography apparatus" can be deemed to be a "photography system".

The present apparatus is configured including a polarization sensitive OCT (PS-OCT) apparatus 100, a polarization sensitive scanning laser opthalmoscope (PS-SLO) 140, an anterior ocular segment photography unit. 160, an interior fixation lamp 170, and a control unit 200.

In a state where the interior fixation lamp 170 is turned on and the eye gazing the interior fixation lamp 170, alignment of the apparatus is performed using an anterior ocular segment image of the eye as observed by the anterior ocular segment photography unit 160. After alignment is completed, fundus photography is performed by the PS-OCT apparatus 100 and PS-SLO 140.

Configuration of PS-OCT Apparatus 100

The configuration of the PS-OCT apparatus 100 will now be described. A light source 101 is a super luminescent diode (SLD) light source which is a type of low-coherence light source. The light source 101 emits light having a center wavelength of 850 nm and a bandwidth of 50 nm, for example. Although an SLD is described as being used for the light source 101, any light source capable of emitting low-coherence light may be used, such as an amplified spontaneous emission (ASE) light source, for example.

The light emitted from the light source 101 is guided to a fiber coupler 104 having polarization-maintaining functions, via a single mode (SM) fiber 134, polarization controller 103, a coupler 135, and a PM fiber 102, and branches into measurement light (hereinafter also referred to as "tomographic image measurement light" or "OCT measurement light"), and reference light corresponding to the measurement light.

The polarization controller 103 adjusts the state of polarization of the light emitted from the light source 101 so as to be adjusted to linearly-polarized light. The branching ratio at the fiber coupler 104 is reference light 90 to measurement light 10.

The measurement light is emitted as parallel light from a collimator 106 via a PM fiber 105. The emitted measurement light passes through an X-scanner 107 made up of a galvano mirror which scans the measurement light in the horizontal direction at a fundus Er, lenses 108 and 109, and a Y-scanner 110 made up of a galvano mirror which scans the measurement light in the vertical direction at the fundus Er, and reaches a dichroic mirror 111. The X-scanner 107 and Y-scanner 110 are controlled by a driving control unit 180, and can scan measurement light over a predetermined range of the fundus Er. Note that the range on the fundus Er where the measurement light is scanned can be deemed to be an acquisition range of a tomographic image, an acquisition position of a tomographic image, and a light-casting position for measurement light. The X-scanner 107 and Y-scanner 110 are examples of scanning units for PS-OCT, and may be configured as a common X-Y scanner. The dichroic mirror 111 has properties where light of 800 nm to 900 nm is reflected, and other light is transmitted.

The measurement light reflected by the dichroic mirror 111 passes via a lens 112 and through a $\lambda/4$ polarization plate 113 inclined at a 45 degrees angle as from p-polarized light to s-polarized light with the optical axis as the rotational axis. Thus the phase is shifted by 90 degrees, so the polarization of the light is controlled to be circularly-polarized light. Note that the term "p-polarized light" as used in the present specification is light which vibrates horizontally as to the face of incidence when the polarization splitting face of the polarization beam splitter is the reflecting face. S-polarized light is light which vibrates perpendicularly to the face of incidence. Note that the polarization plate 113 is an example of a polarization adjusting member for the measurement light, to adjust the polarization state of the measurement light. In a case of applying a later-described PS-SLO optical system, the $\lambda/4$ polarization plate 113 can be provided on a common optical path with a part of a PS-OCT optical system and a part of the PS-SLO optical system. Accordingly, variance in the polarization state occluding in images obtained by the PS-SLO optical system and images obtained by the PS-OCT optical system can be suppressed. A scanning unit for PS-SLO and a scanning unit for PS-OCT are situated in conjugate positions, and can be situated at positions conjugate with the pupil of the eye. Note that the inclination of the $\lambda/4$ polarization plate 113 is one example of the state of the $\lambda/4$ polarization plate 113, and is an angle from a predetermined position, with the optical axis of the polarization splitting face of a fiber coupler 123 including a polarization beam splitter serving as the rotational axis.

The $\lambda/4$ polarization plate 113 also can be configured to be extractably inserted to the optical path. For example, a mechanical configuration where the $\lambda/4$ polarization plate 113 is rotated on the optical axis or an axis parallel to the optical axis can be conceived. This can realize a small apparatus in which the SLO optical system and PS-SLO optical system can be easily switched between. Also, this can realize a small apparatus in which the OCT optical system and PS-OCT optical system can be easily switched between.

Now, the light input to the eye has the polarization thereof controlled to be circularly-polarized light, by the $\lambda/4$ polarization plate 113 being installed at a 45 degree angle. However, there are cases where the light is not circularly-polarized light at the fundus Er, due to properties of the eye. Accordingly, the $\lambda/4$ polarization plate 113 is configured such that the inclination thereof can be fine-adjusted under control of the driving control unit 180.

The measurement light of which the polarization has been controlled to be circularly-polarized light is focused on a retina layer of the fundus Er by a focus lens 114 on a stage 116, via an anterior ocular segment Ea which is the object. The measurement light cast upon the fundus Er is reflected/scatter at each retina layer, and returns on the optical path to the fiber coupler 104.

The reference light which has branched at the fiber coupler 104 passes through a PM fiber 117 and is emitted from a collimator 118 as parallel light. The emitted reference light is subjected to polarization control by a $\lambda/4$ polarization plate 119 inclined at a 22.5 degrees angle as from p-polarized light to s-polarized light, with the optical axis as the rotational axis, in the same way as the measurement light. Note that the $\lambda/4$ polarization plate 119 is an example of a polarization adjusting member for the reference light, to adjust the polarization state of the reference light. The reference light passes through a dispersion compensation glass 120, is reflected at a mirror 122 on a coherence gate stage 121, and returns to the fiber coupler 104. The reference light passes through the λ/4 polarization plate 119 twice, whereby linearly-polarized light returns to the fiber coupler 104.

The coherence gate stage 121 is controlled by the driving control unit 180 to deal with difference in the axial length of the eye of the object, and so forth. Note that a coherence gate is a position corresponding to the optical path length of the reference light in the optical path of the measurement light. While the optical path length of the reference light is changed in the present embodiment, it is sufficient that the optical path length difference between the optical path of the measurement light and the optical path of the reference light is changeable.

The return light which has returned to the fiber coupler 104 and the reference light are multiplexed to form interference light (hereinafter also referred to as "multiplexed light"), which is input to a fiber coupler 123 including a polarization beam splitter, and split into p-polarized light and s-polarized light, which have different polarization directions, at a branching ratio of 50 to 50.

The p-polarized light passes through a PM fiber 124 and collimator 130, is dispersed at grating 131, and received at a lens 132 and line camera 133. In the same way, the s-polarized light passes through a PM fiber 125 and collimator 126, is dispersed at grating 127, and received at a lens 128 and line camera 129. Note that the grating 127 and 131, and line cameras 129 and 133 are positioned in accordance to each polarization direction.

The light received at each of the line cameras 129 and 133 is output as electric signals in accordance to the intensity of light, and received at the signal processing unit 190.

The inclination of the λ/4 polarization plates 113 and 119 can be automatically adjusted with reference to the inclination of the polarization splitting face of the polarization beam splitter included in the fiber coupler 123. At this time, an inclination detector (not illustrated) which detects the inclination of the λ/4 polarization plates 113 and 119 is preferably provided. This inclination detector can detect whether the current inclination matches a predetermined inclination. Of course, the degree of inclination of the λ/4 polarization plates 113 and 119 can be detected based on the intensity of light that has been received, and adjusted so that the intensity is a predetermined intensity. Also, as described later, the user may display objects indicating inclination on a graphical user interface (GUI) and perform adjustments using a mouse. Also, the same effects can be obtained by adjusting the polarization beam splitter and λ/4 polarization plates 113 and 119 with the vertical direction as the reference.

Configuration of PS-SLO 140

The configuration of the PS-SLO 140 will now be described. A light source 141 is a semiconductor layer which emits light having a center wavelength of 780 nm, for example, in the present embodiment. The measurement light emitted from the light source 141 (hereinafter also referred to as "measurement light for fundus image" or "SLO measurement light") passes through a PM fiber 142, the polarization thereof is controlled at a polarization controller 145 so as to become linearly-polarized light, and is output from a collimator 143 as parallel light. The emitted measurement light passes through the perforation of a perforated mirror 144, passes through a lens 155, passes through an X-scanner 146 made up of a galvano mirror which scans the measurement light in the horizontal direction at a fundus Er, lenses 147 and 148, and a Y-scanner 149 made up of a galvano mirror which scans the measurement light in the vertical direction at the fundus Er, and reaches a dichroic mirror 154. The X-scanner 146 and Y-scanner 149 are controlled by the driving control unit 180, and can scan measurement light over a predetermined range of the fundus Er. The X-scanner 146 and Y-scanner 149 are examples of scanning units for PS-SLO, and may be configured as a common X-Y scanner. The dichroic mirror 154 has properties where light of 760 nm to 800 nm is reflected, and other light is transmitted.

The linearly-polarized light measurement light reflected at the dichroic mirror 154 passes over the same optical path as with the PS-OCT apparatus 100, and reaches the fundus Er.

The measurement light which has been cast on the fundus Er is reflected/scatter at the fundus Er, and returns on the above-described optical path to reach the perforated mirror 144. The light reflected at the perforated mirror 144 passes through a lens 150 and is input to a polarization beam splitter 151, and it into light which have different polarization directions (p-polarized light and s-polarized light in the present embodiment), received at avalanche photodiodes (APD) 152 and 153 and converted into electric signals, which are received at the signal processing unit 190.

The position of the perforated mirror 144 is conjugate with the pupil position of the eye. Of the measurement light cast on the fundus Er and reflected/scattered, the light which has passed through around the pupil is reflected by the perforated mirror 144.

While PM fibers have been used for both the PS-OCT apparatus and PS-SLO in the present embodiment, the same configuration and effects can be obtained by controlling polarization using a polarization controller even if using single mode fiber (SMF).

Anterior Ocular Segment Photography Unit 160

The anterior ocular segment photography unit 160 will now be described. The anterior ocular segment photography unit 160 illuminates the anterior ocular segment Ea using an illumination light source 115 including LEDs 115-a and 115-b which emit illumination light having a wavelength of 1000 nm. The light reflected at the anterior ocular segment Ea passes through the lens 114, polarization plate 113, lens 112, dichroic mirrors 111 and 154, and reaches a dichroic mirror 161. The dichroic mirror 161 has properties where light of 980 nm to 1100 nm is reflected, and other light is transmitted. The light reflected at the dichroic mirror 161 passes through lenses 162, 163, and 164, and is received at an anterior ocular segment camera 165. The light received at the anterior ocular segment camera 165 is converted into electric signals, and received at the signal processing unit 190.

Interior Fixation Lamp 170

The interior fixation lamp 170 will now be described. The interior fixation lamp 170 is configured including an interior fixation lamp display unit 171 and a lens 172. The interior fixation lamp display unit 171 includes multiple light-emitting diodes (LEDs) arrayed in a matrix. The lighting position of the LEDs is changed in accordance with the region to be photographed, under control of the driving control unit 180. Light from the interior fixation lamp display unit 171 is guided to the eye via the lens 172. The light emitted from the interior fixation lamp display unit 171 has a wavelength of 520 nm, and a desired pattern is displayed by the driving control unit 180.

Control Unit 200

The control unit 200 which controls the overall apparatus will now be described. The control unit 200 includes the driving control unit 180, the signal processing unit 190, a display control unit 191, and a display unit 192. The driving control unit 180 controls each part as described above.

The signal processing unit 190 includes an image generating unit 193, an image analyzing unit 194, an image overlaying unit 195, and a comparing unit 196. The signal processing unit 190 generates images, analyzes the generated images, and generates visualization information of the analysis results, based on signals output from each of the line cameras 129 and 133, APDs 152 and 153, and anterior ocular segment camera 165. Details of generating and analyzing images will be described later.

The display control unit 191 displays fundus images, fundus tomographic images, and so forth, generates at the signal processing unit 190, on a display screen of the display unit 192. The display unit 192 here is a liquid crystal display or the like. The image data generated at the signal processing unit 190 may be transmitted to the display control unit 191 by cable, or wirelessly. In this case, the display control unit 191 can be deemed to be an image processing apparatus, and it is sufficient that the image processing apparatus and photography apparatus (ophthalmologic apparatus) are communicably connected. An arrangement may be made for the photography system where a fundus image acquisition unit includes an SLO optical system, and a tomographic image acquisition unit includes an OCT optical system. In the present Specification, if the object is other than an eye, the term "fundus image (fundus luminesce image)" can be rephrased as "planar image "planar luminesce image)", and the term "fundus image acquisition unit" can be rephrased as "planar image acquisition unit".

The display unit 192 displays various types of information in various display formats under control of the display control unit 191, as described later. The image data from the display control unit 191 may be transmitted to the display unit 192 by cable, or wirelessly. While the display unit 192 and other units are illustrated as being included in the control unit 200, but the present invention is not restricted to this, and may be provided separately from the control unit 200. Also, the display control unit 191 and display unit 192 may be integrally formed as a tablet, which is an example of a device which can be carried by the user. In this case, the display unit preferably has a touch panel function, so that the display position can be moved, enlarged, or reduced, and the displayed image can be changed, or the like, by performing operations on the touch panel.

Image Processing

Next, image generating at the image generating unit 193 included in the signal processing unit 190 will be described. The image generating unit 193 performs reconstruction processing commonly used in spectral domain (SD) OCT on interference signals output from the line cameras 129 and 133, thereby generating two tomographic images based on each polarization component. The two tomographic images are a tomographic luminance image corresponding to first polarization light, and a tomographic luminance image corresponding to second polarization light.

First, the image generating unit 193 removes fixed pattern noise from the interference signals. Removal of the fixed pattern noise is performed by extracting the fixed pattern noise by averaging multiple A-scan signals that have been detected and subtracting the fixed pattern noise from the input interference signals.

Next, the image generating unit 193 converts the interference signals from wavelength to wavenumber, and performs Fourier transform, thereby generating tomography signals representing the polarization state.

Performing the above-described processing on the interference signals of the two polarization components generates two tomographic luminance images.

The image generating unit 193 arrays the signals output from the APDs 152 and 153 synchronously with the driving of the X-scanner 146 and Y-scanner 149, thereby generating two fundus images based on the respective polarization components. The two fundus images are a fundus image corresponding to the first polarization light, and a fundus image corresponding to the second polarization light.

Generating Tomographic Luminance Image or Fundus Luminance Image

The image generating unit 193 generates a tomographic luminance image from the two aforementioned tomography signals. The tomographic luminance image is basically the same as a tomographic images in conventional OCT. A pixel value r thereof is calculated from tomography signals $A_H$ and $A_V$ obtained from the line sensors 129 and 133, as calculated by Expression (1).

[Math. 1]

$$r = \sqrt{A_H^2 + A_V^2} \qquad \text{Expression (1)}$$

A fundus luminance image is also generated from the two fundus images in the same way.

Figure 2A:
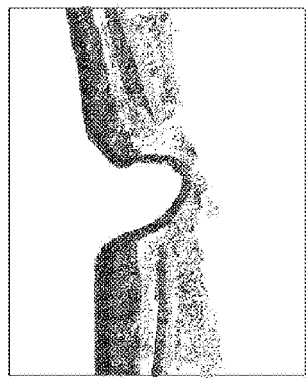
FIGS. 2A through 2E are examples of images generated at a signal processing unit according to the first embodiment.

FIG. 2A illustrates an example of a luminance image of an optic disc. The display control unit 191 may display a tomographic luminance image acquired by conventional OCT techniques on the display unit 192 in a case where the λ/4 polarization plate 113 has been evacuated from the optical path, or may display a fundus luminance image acquired by conventional SLO techniques on the display unit 192.

Generating Retardation Image

The image generating unit 193 generates retardation images from tomographic images of mutually orthogonal polarization components. A value δ of each pixel of the retardation image is a value representing the ratio of influence which the vertical polarization component and horizontal polarization component receive at the eye, at the position of each pixel in the tomographic image. The value δ is calculated from the tomography signals $A_H$ and $A_V$ by the following Expression (2).

[Math. 2]

$$\delta = \arctan\left[\frac{A_V}{A_H}\right] \qquad \text{Expression (2)}$$

Figure 2B:
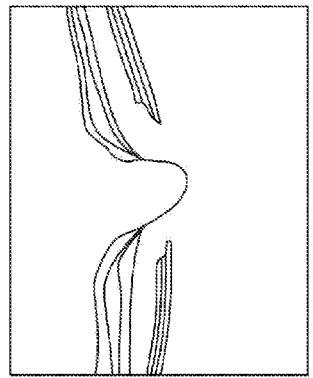

FIG. 2B illustrates an example of a retardation image of the optic disc generated in this way, and can be obtained by performing calculation according to Expression (2) on each B-scan image. As described earlier, a retardation image is a tomographic image indicating the difference in influence which the two polarization components received at the eye. FIG. 2B is a color display to values representing the above ratio as a tomographic image. Dark portions indicate a small value for the ratio, and light portions indicate a great value for the ratio. Accordingly, layers with birefringence can be comprehended by generating a retardation image. Details are described in NPL 1.

The image generating unit. 193 can generate a retardation image in the planar direction of the fundus, based on output from the APDs 152 and 153 in the same way.

Generating Retardation Map

The image generating unit 193 generates a retardation map from the retardation image obtained with regard to multiple B-scan images. The image generating unit 193 detects the retinal pigment epithelium (RPE) in each B-scan image. The RPE has a nature of cancelling polarized light, so retardation distribution is inspected in each A-scan image in the depth direction, from the inner limiting membrane (ILM) over a range not including the RPE. The maximum value thereof is the representative value of retardation in the A-scan.

The image generating unit 193 performs the above processing on all retardation images, thereby generating a retardation map.

Figure 2C:
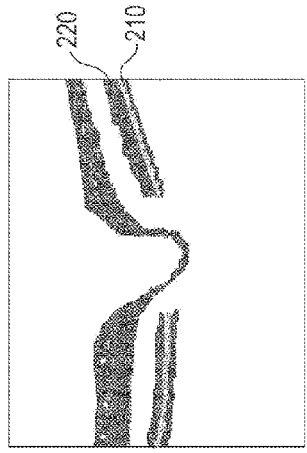

FIG. 2C illustrates an example of a retardation map of the optic disc. Dark portions indicate a small value for the aforementioned ratio, and light portions indicate a great value for the aforementioned ratio. The retinal nerve fiber layer (RNFL) is a layer having birefringence at the optic disc. The retardation map is an image illustrating the difference in influence which the two polarized lights receive due to the birefringence of the RNFL and the thickness of the RNFL. Accordingly, in a case where the density of the retinal nerve fibers is uniform, the value indicating the aforementioned ratio is great when the RNFL is thick, and the value indicating the aforementioned ratio is small when the RNFL is thin.

Generating Birefringence Map

The image generating unit 193 linearly approximates the value of retardation $\delta$ in the range of the ILM to the RNFL, in each A-scan image of the retardation images generated earlier, and determines the inclination thereof to be the birefringence at the position of the A-scan image on the retina. That is to say, the retardation is the product of distance and birefringence in the RNFL, so a linear relation is obtained by plotting the depth and retardation values in each A-scan image. Accordingly, this plot is subjected to linear approximation by the method of least squares, and the inclination is obtained, which is the value for birefringence of the RNFL in this A-scan image. This processing is performed on all retardation images that have been acquired, thereby generating a map representing birefringence.

Figure 2D:

FIG. 2D illustrates an example of a birefringence map of the optic disc. The birefringence map directly maps birefringence values, so even if the thickness of the RNFL does not change, change in the fiber structure thereof can be visualized as change in birefringence.

Generating a DOPU Image

The image generating unit 193 calculates a Stokes vector S for each pixel, from the obtained tomography signals $A_H$ and $A_V$, and the phase difference $\Delta\Phi$ therebetween, by the following Expression (3),

[Math. 3]

$$S = \begin{pmatrix} I \\ Q \\ U \\ V \end{pmatrix} = \begin{pmatrix} A_H^2 + A_V^2 \\ A_H^2 - A_V^2 \\ 2A_H A_V \cos\Delta\phi \\ 2A_H A_V \sin\Delta\phi \end{pmatrix} \quad \text{Expression (3)}$$

where $\Delta\Phi$ has been calculated from $\Delta\Phi = \Phi_V - \Phi_H$, from the phases $\Phi_H$ and $\Phi_V$ of each signal obtained at the time of calculating the two tomographic images.

The image generating unit 193 sets a window for each B-scan image of a size around 70 μm in the main scanning of the measurement light and 18 μm the depth direction, averages each element of the Stokes vector calculated for each pixel within each window, and calculates the degree of polarization uniformity (DOPU) in each window by Expression (4),

[Math. 4]

$$\text{DOPU} = \sqrt{Qm^2 + Um^2 + Vm^2} \quad \text{Expression (4)}$$

where $Q_m$, $U_m$, and $V_m$ are each values of the averaged Stokes vector elements Q, U, and V in each window.

Figure 2E:
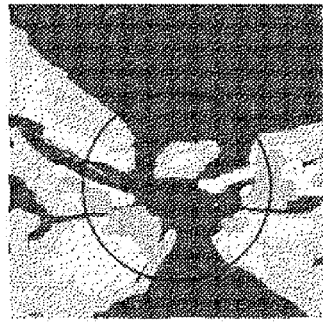

This processing is performed on all windows within the B-scan image, thereby generating a DOPU image of the optic disc illustrated in FIG. 2E. As described above, a DOPU image is a tomographic image indicating the uniformity of the two polarized lights.

DOPU is a numerical value representing uniformity of polarized light. At locations where polarization is maintained, the value is near 1, and the value is smaller than 1 at locations where polarization is cancelled and not maintained. The RPE has a nature of cancelling the polarization state, so the portions in the DOPU image corresponding to the RPE exhibit a smaller value as compared to other regions. The light portion 210 in FIG. 2E represents the RPE, and the dark portion 220 represents the retinal layer region where polarization is maintained. The DOPU image visualizes layers where polarization is cancelled, such as the RPE and so forth, so even in a case where the RPE has been deformed by a disease or the like, the RPE can be visualized in a more sure manner than change in luminance.

Also, in the same way, the image generating unit 193 can generate a DOPU image in the planar direction of the fundus, based on output from the APDs 152 and 153.

Note that in the present Specification, the above-described tomographic luminance images corresponding to the first and second polarized light, retardation images, DOPU images, and so forth, may also be referred to as "tomographic images indicating polarization state" or "polarization-sensitive tomographic images". Also in the present Specification, the above-described retardation map and birefringence map and so forth may also be referred to as "fundus image indicating polarization state" or "polarization fundus image".

The image analyzing unit 194 which is an example of an extracting unit can extract (detect), from a tomographic image indicating polarization state such as a DOPU image or retardation image or the like, a region (location) where polarization has been cancelled, such as the RNFL or the like. The image analyzing unit 194 can also identify regions where polarization has been canceled than have a particular shape as being a pathological site. An example of a region where polarization has been cancelled is a region where difference in influence which the two polarized lights receive at the eye is relatively great.

Processing Operations

Next, processing operations according to the image processing apparatus will be described. FIG. 3 is a flowchart illustrating processing operations of the image processing apparatus.

Adjustment

First, in step S101, alignment of the apparatus and eye is performed with the eye set to the apparatus. Description will be made regarding alignment unique to the present specification, and general adjustments such as XYZ alignment of working distance and so forth, focusing, coherence gate adjustment, and so forth will be omitted from description.

Adjustment of PS-OCT Photography Position

Figure 4:
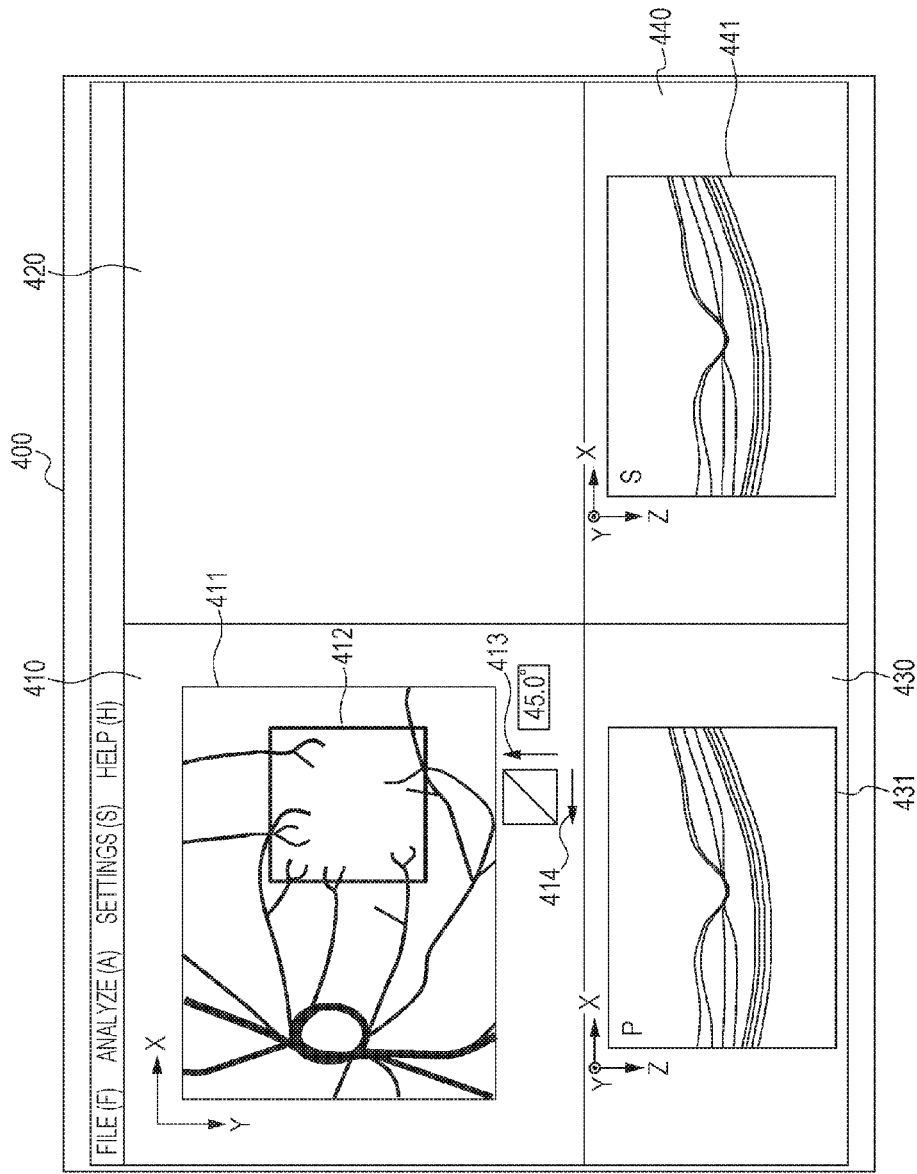
FIG. 4 is a display example of a display screen on a display unit of the image processing apparatus according to the first embodiment.

FIG. 4 illustrates a window 400 displayed on the display unit 192 when performing adjustments. A display region 410 which is an example of a first display region displays a fundus image 411 taken by the PS-SLO 140 and generated by the image generating unit 193. A guide 412 indicating the photography position of the PS-OCT apparatus 100 is superimposed thereupon.

The operator sets a photography range by instructing using a cursor displayed in the window 400, by performing clicking and dragging operations and the like on an instruction device such as a mouse or the like (not illustrated), or by directly specifying in a numerical value input space provided to the window 400. Setting of the photography range is performed under control of the driving control unit 180. Thus, the driving control unit 100 sets the photography range for controlling the driving angle of the scanner. The mouse in this embodiment includes, for example, a sensor to detect motion signals when the mouse is moved two-dimensionally by the hand of the user, two mouse buttons, left and right, to detect pressing by the hand of the user, and a wheel mechanism which is provided between the two left and right mouse buttons and which can be rotated forwards and backwards. The instruction device may be such that a display unit is provided with touch panel functions, so that acquisition positions are specified on the touch panel.

Adjustment of λ/4 Polarization Plate

Adjustment of the λ/4 polarization plate 113 will be described. In FIG. 4, instruction portions 413 and 414 are displays to adjust the angle of the λ/4 polarization plate 113. The angle of the λ/4 polarization plate 113 is adjusted by the operating giving instructions using the instruction device, under control of the driving control unit 180. The instruction portion 413 is a display for instructing adjustment in the counter-clockwise direction, and the instruction portion 414 is a display for instructing adjustment in the clockwise direction. The numerical value displayed to the side of the instruction portions 413 and 414 indicates the current angle of the λ/4 polarization plate 113. The display control unit 191 may display instruction portions for adjusting the angle of the λ/4 polarization plate 119 alongside the instruction portion 413 on the display unit 192, or instead of the instruction portion 413.

Guiding the cursor by the mouse, the operator input instructions so that the luminance of each tomographic luminance image displayed in a display region 430 which is an example of a third display region, and a display region 440 which is an example of a fourth display region, are the same. This may be done by displaying the peak luminance values of the tomographic luminance images 431 and 441 of the respective polarized lights, or by displaying waveforms themselves of the interference signals, and the operator viewing these and performing adjustment. Here, the tomographic luminance images 431 and 441 of the respective polarized lights are examples of a tomographic luminance image corresponding to first polarized light and a tomographic luminance image corresponding to second polarized light. The tomographic luminance images 431 and 441 of the respective polarized lights preferably are of a display format indicating the type of image, such as indicating p-polarized light and "S" indicating s-polarized light being superimposed on the images, for example. This helps to prevent the user from misidentifying the images. Of course, this display may be made above or to the side of the images instead of being superimposed, as long as correlated with the images.

A display region 420 which is an example second display region may display nothing at this stage, or in the case of automatic adjustment or the like may display a message such as "Currently adjusting λ/4 polarization plate" or the like to indicate the current adjustment state. Also, the window 400 may display patient information such as the eye and the other eye of the left and right eyes, photography information such as the photography mode and so forth, or the like. The λ/4 polarization plate 113 is preferably repetitively inserted into and evacuated from the optical path, so as to alternately obtain fundus luminance images and tomographic luminance images indicating polarization state. This enables the display control unit 191 to display a fundus luminance image in the display region 410, and then display a tomographic luminance image indicating polarization state in the display region 420, using an ophthalmologic apparatus of which the size is minimal.

The order of adjustment preferably is alignment adjustment using anterior ocular segment images or corneal bright, points, focus adjustment using fundus images indicating polarization state, coherence gate adjustment using tomographic luminance images indicating polarization state, and adjustment of the λ/4 polarization plate 113. While the acquisition position of the tomographic luminance image indicating polarization state is preferably performed before the coherence gate adjustment using tomographic luminance images indicating polarization state, this may be decided at in initial settings so as to acquire the center region of the fundus image indicating polarization state. Accordingly, tomographic luminance images indicating polarization state which can handle finer and narrower ranges than fundus images indicating polarization state can be accurately acquired by simple adjustment. At this time, the λ/4 polarization plate 113 may be automatically adjusted in accordance with completion of the coherence gate adjustment, or the λ/4 polarization plate 113 may be automatically adjusted in accordance with input of a signal to acquire an image indicating polarization state. Of course, a configuration may be made where the λ/4 polarization plate 113 is adjusted at the initial settings screen upon startup of the ophthalmologic apparatus, and not adjusted each time photography is performed.

In a case where the λ/4 polarization plate 113 is configured to be inserted and evacuated from the optical path, the order of adjustment preferably is alignment adjustment using anterior ocular segment images or corneal bright points, focus adjustment using SLO fundus images, coherence gate adjustment using OCT tomographic luminance images, insertion of the λ/4 polarization plate 113 into the optical path, and adjustment of the λ/4 polarization plate 113. Thus, adjustment before acquiring images indicating polarization state can be performed using normal SLO fundus images and OCT tomographic luminance images which the user is intuitively familiar with. Alternatively, the λ/4 polarization plate 113 may be inserted after focus adjustment, and thereafter coherence gate adjustment performed using a PS-OCT tomographic luminance image indicating polarization state. In this case, the λ/4 polarization plate 113 may be automatically inserted into the optical path in accordance with completion of the coherence gate adjustment or completion of focus adjustment, or the λ/4 polarization plate 113 may be automatically inserted into the optical path in accordance with input of a signal to acquire an image indicating polarization state.

The focus adjustment may be performed such that rough focus adjustment is first performed using an SLO fundus image, and thereafter fine focus adjustment is performed using an OCT tomographic luminance image.

These adjustments may be performed in the above-described order automatically, or sliders may be displayed on the display unit corresponding to each adjustment, and the cursor used to perform drag operations for adjustment. In a case of inserting/evacuating the λ/4 polarization plate 113, icons to insert the λ/4 polarization plate 113 into the optical path, and to evacuate, may be displayed on the display unit.

Fundus Photography Through Generating Fundus Images

In steps S102 and S103, measurement light is emitted from the light source 141, and return light from the fundus Er is received at the APBs 152 and 153, so as to generate the fundus image at the image generating unit 193 as described above. The comparing unit 196 records acquired fundus data.

Setting OCT Scan Position

In step S104, the fundus images taken in steps S102 and S103 are compared with fundus images taken and acquired in the past, and a scan position for the PS-OCT apparatus 100 is set.

First, the comparing unit 196 extracts position information of feature points in fundus images taken and acquired in the past. Two or more feature points are preferably extracted, since the scan direction cannot be matched with only one point. Feature points are tissue such as the optic disc, maculae, capillaries, and the like. Next, relative position information of OCT scans acquired and recorded in the past are calculated as to the position information of the feature points that have been extracted. The feature points of a fundus image currently acquired and recorded are extracted in the same way as above, and then matching points with the feature points extracted from the past fundus images are further extracted. Finally, the OCT scan position is set based on the position information of the feature points extracted form the current fundus image and the relative position information that has been calculated.

Figure 5:
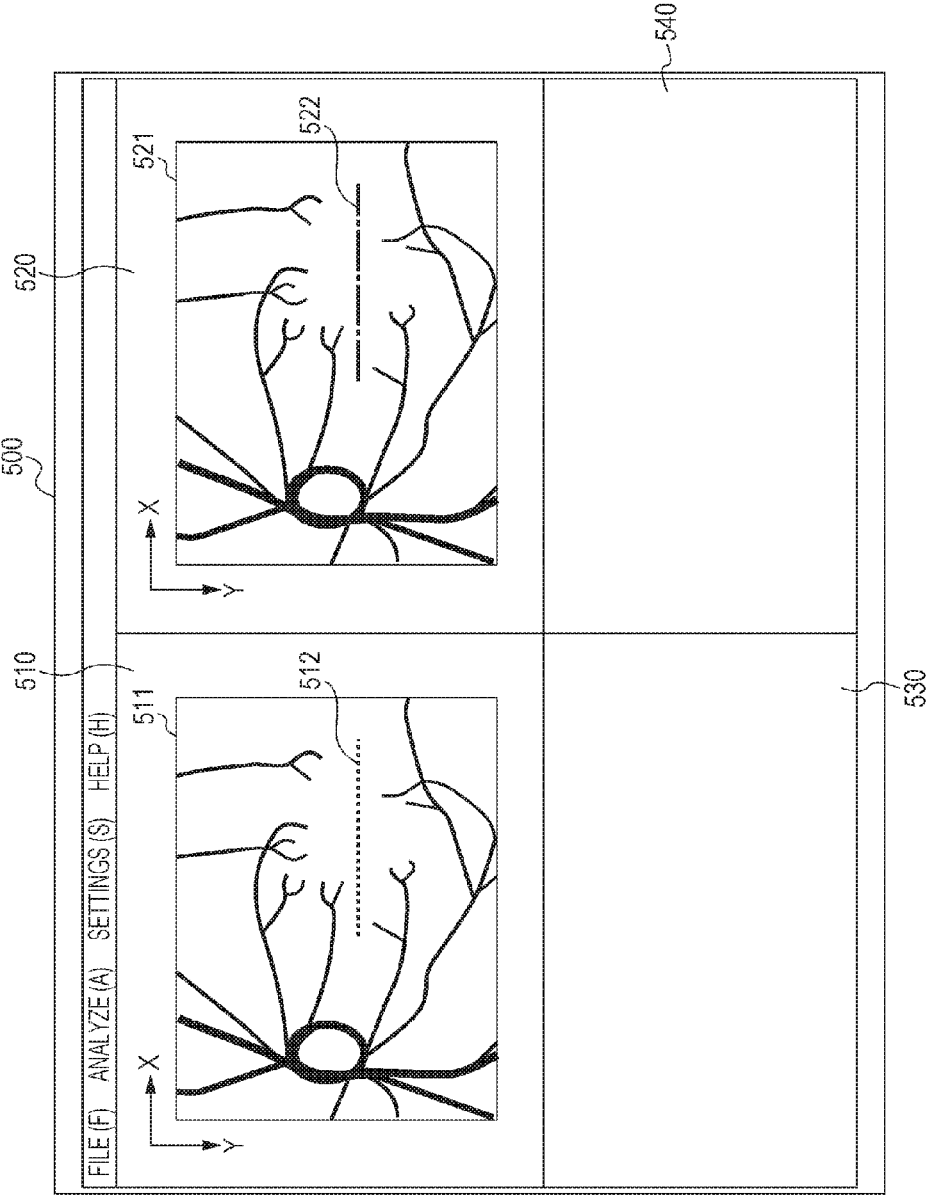
FIG. 5 is an explanatory diagram of positioning an OCT scan position according to the first embodiment.

Note that the OCT scan position is not restricted to the automatic extraction described above. Selection may be manually made from a window, as illustrated in FIG. 5.

A display region 510, which is an example of a first display region, displays a current fundus image 511 taken by the PS-SLO 140 and generated by the image generating unit 193. A fundus luminance image is illustrated here as the fundus image 511, but this may be a fundus image based on polarization signals. A guide 512 indicating the photography position of the PS-OCT apparatus 100 is displayed superimposed on the fundus image 511.

A display region 520, which is an example of a second display region, displays a past fundus image 521 taken by the PS-SLO 140 and generated by the image generating unit 193. A fundus luminance image is illustrated here as the fundus image 521, but this may be a fundus image based on polarization signals. A guide 522 indicating the photography position of the PS-OCT apparatus 100 which performed the image photography in the past is displayed superimposed on the fundus image 521.

The OCT scan position is set with the guide 512 superimposed on the fundus image 511 displayed in the display region 510 by clicking and dragging operations and the like of the mouse, so as to correspond to the positional relation of a past fundus image 521 displayed in the display region 520 and the guide 522 displayed on the fundus image 521.

Tomography Shooting Through Generating of Tomographic Luminance Image

In steps S105 and S106, measurement light is emitted from the light source 101, return light from the fundus Er is received at the line cameras 129 and 133, and a tomographic luminance image is generated at the image generating unit 193 as described above.

The steps S105 and S106 are repeated N times as to the tomographic luminance image position that has been set, thereby acquiring N tomographic luminance images. Alternatively, the acquisition procedures may be optionally decided by the operator. That is, step S106 may be performed in batch fashion after having repeated step S105 N times and obtained the data of N tomographic luminance images, or steps S105 and S106 may be performed in order for each acquisition of a tomographic luminance image, and this may be repeated N times.

Also, steps S102 and S103 may be performed in parallel at an optional timing while performing the shooting and generating of the tomographic luminance images in steps S105 and S106, fine movement amount of SLO images detected at the signal processing unit 190, and feedback performed at the driving control unit 180, thereby imparting a tracking function. For example, in one method, consecutively acquired SLO image data is handed to the signal processing unit 190, and fine movement amount in translation direction or rotational direction with regard to a relative position in the SLO images is calculated. Next, a scanner driving waveform to correct the calculated fine movement amount is generated at the driving control unit 180, and the X-scanner 107 and Y-scanner 110 are driven to realize the tracking function.

Overlaying OCT Tomographic Images

Figure 6A:
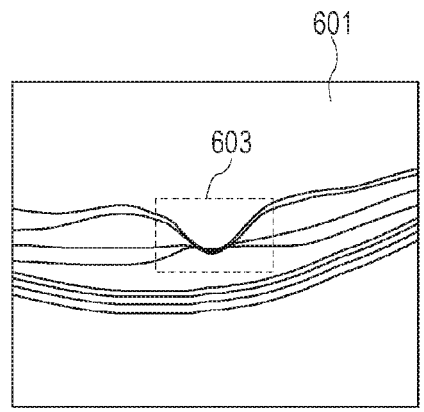
FIGS. 6A and 6B are explanatory diagrams of positioning, when overlaying tomographic luminance images according to the first embodiment.
Figure 6B:
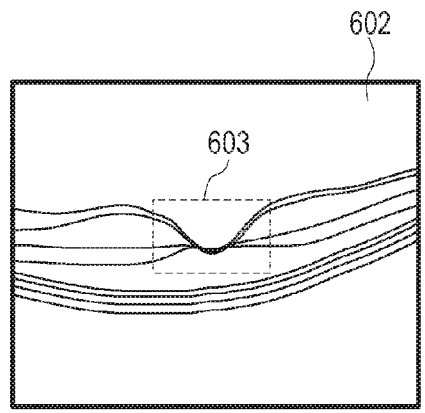

After photograph and image processing of the N images, in step S107 the image overlaying unit 195 which is an example of a position overlaying device first positions the multiple tomographic luminance images. The method for positioning will now be described with reference to FIGS. 6A and 63. Positioning of the multiple tomographic luminance images is performed by first detecting eye movement, by performing pattern matching of a second luminance image 602 as to a reference first luminance image 601. Pattern matching is a technique to search for a region where similarity as to a reference image is the highest. An arrangement may be made where a feature portion is extracted from the first luminance image serving as a reference, and pattern matching is performed as to the second luminance image, searching for a location which matches or the similarity is the highest, and eye movement during the image acquisition period is detected from the coordinates thereof. A macula 603 in the luminance image 601 may be used to perform pattern matching, for example.

This pattern matching is performed at the image overlaying unit 195, and the similarity of multiple other luminance images as to the reference first luminance image is calculated. A correlation function may be used for calculating similarity, for example.

In the present embodiment, in a case of overlaying N tomographic luminance images at the same location of the object for example, pattern matching may be performed so that each image of N−1 luminance images have the highest similarity as to the first luminance image. Displaying similarity as a parameter at the time of performing pattern matching enables this to be used as an indicator of whether or not to overlay, when overlaying the tomographic luminance images. That is to say, by displaying similarity, the user can decide not to use tomographic luminance images with low similarity.

Figure 7:
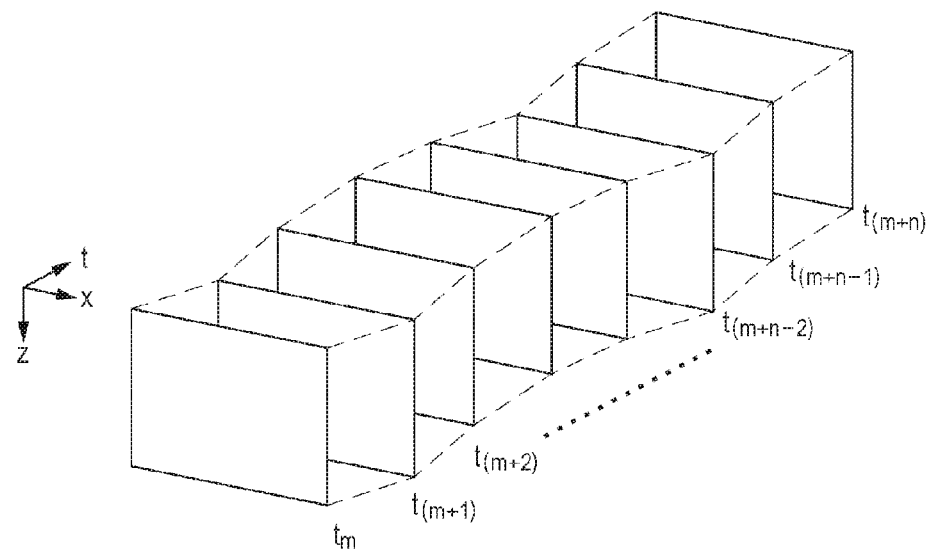
FIG. 7 is a conceptual diagram of overlaying tomographic luminance images according to the first embodiment.

After performing pattern matching, the image overlaying unit 195 stores displacement amount regarding movement of the luminance image which was performed to obtain the highest similarity. For example, in FIG. 7, in a case where (x(m+1), y(m+1)) is amount of displacement of the luminance image of which the similarity is the highest at time t(m+1), as to the luminance image at time tm, this displacement (x(m+1), y(m+1)) is stored. The amount of displacement to be stored here is not restricted to parallel movement. For example, the amount of displacement regarding rotation and enlargement/reduction may be stored as necessary. Also, the displacement amount stored in the image overlaying unit 195 may be applied to all images obtained at the same timing and generated at the image generating unit 193.

The image overlaying unit 195 performs the above-described deformation on each of the tomographic luminance images generated by the image generating unit 193 to average the pixels at the same position in the deformed images, thereby generating an overlaid image. At this time, the positional shift of the multiple tomographic luminance images is preferably corrected based on the detected eye movement. Also, tomographic luminance images where a predetermined luminesce amount is not obtained, due to blinking, are preferably excluded from the overlaid image. Upon the overlaying processing ending, the display control unit 191 generates output information, and outputs to the display unit 192 for display. Also, the comparing unit 196 records the overlaid image data that has been generated.

Comparing

In step S108, a past tomographic luminance image 831 generated by past acquisition and overlaying, and a current tomographic luminance image 841 generated by current acquisition and overlaying, are compared by performing subtraction processing of retardation at corresponding pixels. To this end, the past tomographic luminance image 831 and the current tomographic luminance image 841 are first positioned for comparison. This positioning is performed by deforming the current tomographic luminance image 841 by subjecting to processing such as affine transform so that the correlation function is the highest as compared to the past tomographic luminance image 831. At this time, common regions of the past tomographic luminance image 831 are also extracted and deformed, so as to display the same region as the current tomographic luminance image 841 which is being deformed. Note that both of the deformed past tomographic luminance image 831 and the current tomographic luminance image 841 are reconstructed by performing interpolation regarding luminance values of each pixel and polarization parameters. Examples of interpolation methods include nearest neighbor interpolation, bilinear interpolation, bicubic interpolation, or the like. Note that in the present invention, it is sufficient for the past tomographic image and current tomographic image to be multiple tomographic images obtained by shooting the object at different times.

Figure 8:
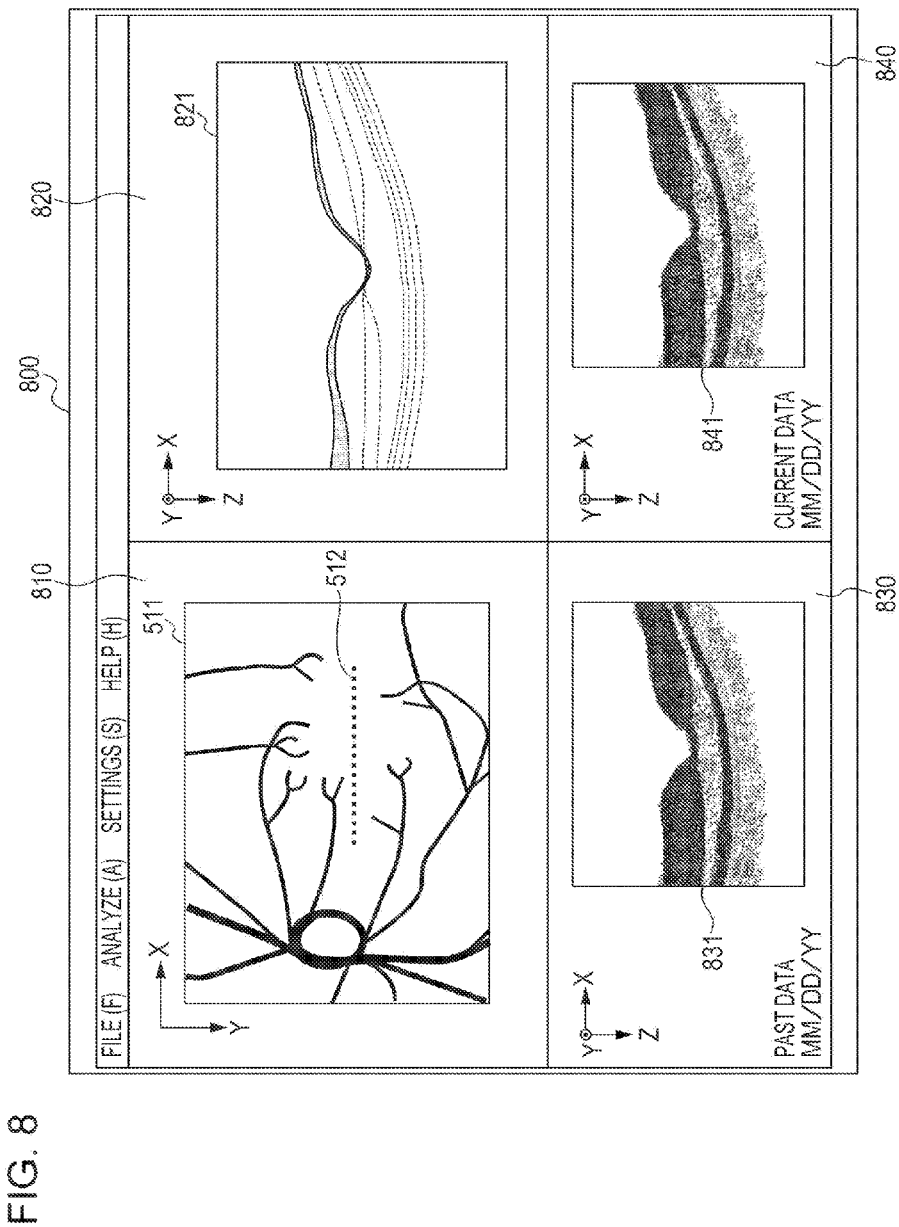
FIG. 8 is a display example of a display screen on the display unit of the image processing apparatus according to the first embodiment.

Next, the comparing unit 196, which is an example of a difference information generating unit, performs comparison by subtracting retardation in the corresponding pixels the past tomographic luminance image 831 and the current tomographic luminance image 841. That is to say, the difference information generating unit generates information indicating the difference between a past polarization-sensitive tomographic image corresponding to the past tomographic luminance image 831 and a current polarization-sensitive tomographic image corresponding to the current tomographic luminance image 841. Examples of information indicating difference include a difference image, a graph indicating difference, and difference values. Before generating the information indicating difference, the past polarization-sensitive tomographic image and the current polarization-sensitive tomographic image are positioned, based on the past tomographic luminance image and the current tomographic luminance image. Thus, positioning of the polarization-sensitive tomographic images can be performed at a region other than the region where polarization has been cancelled, which is an example of the predetermined region. Accordingly, even if the region where polarization is canceled has changed over time due to disease or the like, accurate positioning can be performed. At this time, the positional shift of the multiple polarization-sensitive tomographic images as to the multiple tomographic luminance images is preferably corrected based on the detected eye movement. The subtraction results are displayed in a display region 820 as a difference image 821, as illustrated in FIG. 8. The change over time of density in the RNFL can be tracked by reading the obtained results of subtraction processing. For example, regions where the subtraction value is a positive value indicate that birefringence has weakened, and regions where the subtraction value is a negative value indicate that birefringence has increased. While an example has been illustrated of subtracting retardation which is an example of a current polarization-sensitive tomographic image corresponding to the current tomographic luminance image 841, from retardation which is an example of a past polarization-sensitive tomographic image corresponding to the past tomographic luminance image 831, the present embodiment is not restricted to this arrangement. An arrangement may be made where retardation corresponding to the past tomographic luminance image 831 is subtracted from retardation corresponding to the current tomographic luminance image 841. In this case, regions where the subtraction value is a negative value indicate that birefringence has weakened, and regions where the subtraction value is a positive value indicate that birefringence has increased.

Also in step S108, the current thickness information of the RNFL and the retardation information of the RNFL are each measured and recorded. The operator can optionally select the thickness information of the RNFL and the retardation information. The thickness information of the RNFL can be obtained by obtaining values for each N-coordinate, by calculating the difference in Z components at two points having the same X-coordinates, from the coordinate values of two boundary lines indicating the RNFL extracted by segmentation. Of the thickness data thus obtained, thickness data at an optional X-coordinate, or an average value of thickness data over an optional X-coordinate section, is taken as the RNFL thickness information.

Alternatively, RNFL retardation information is obtained as retardation within the RNFL on an A-scan line corresponding to the X-coordinate where the thickness information is obtained, or the average value of retardation.

Output

Next, the output processing step S109 of the generated images and the analyzed results will be described. The output processing in the present embodiment involves displaying the images acquired and generated, and the results of comparison made, in steps S102 through. S108.

Upon generating, analyzing, and overlaying of the images at the image generating unit 193, image analyzing unit 194, and image overlaying unit 195 of the signal processing unit 190 ending, the display control unit 191 generates output information based on the results thereof, and outputs to the display unit 192 for display.

FIG. 8 is a display example of the display portion 192 according to the present embodiment. In FIG. 8, reference numeral 800 denotes the window where the display portion 192 is displayed, and display regions 810, 820, 830, and 840 are included.

The display region 810 which is an example of a first display region displays a fundus image 511 taken by the PS-SLO 140 and generated by the image generating unit 193. While a fundus luminance image is displayed for the fundus image 511, this may be a fundus image based on polarization signals. A guide 522 indicating the photography position of the PS-OCT apparatus 100 which has shot an image is superimposed on the fundus image 511.

The display region 820 which is an example of a second display region displays the difference in reduction between past and current acquired images at generally the same position, as a topography image 821. Segmentation may be superimposed in addition to the difference image at this time, to clarify each layer.

Figure 9:
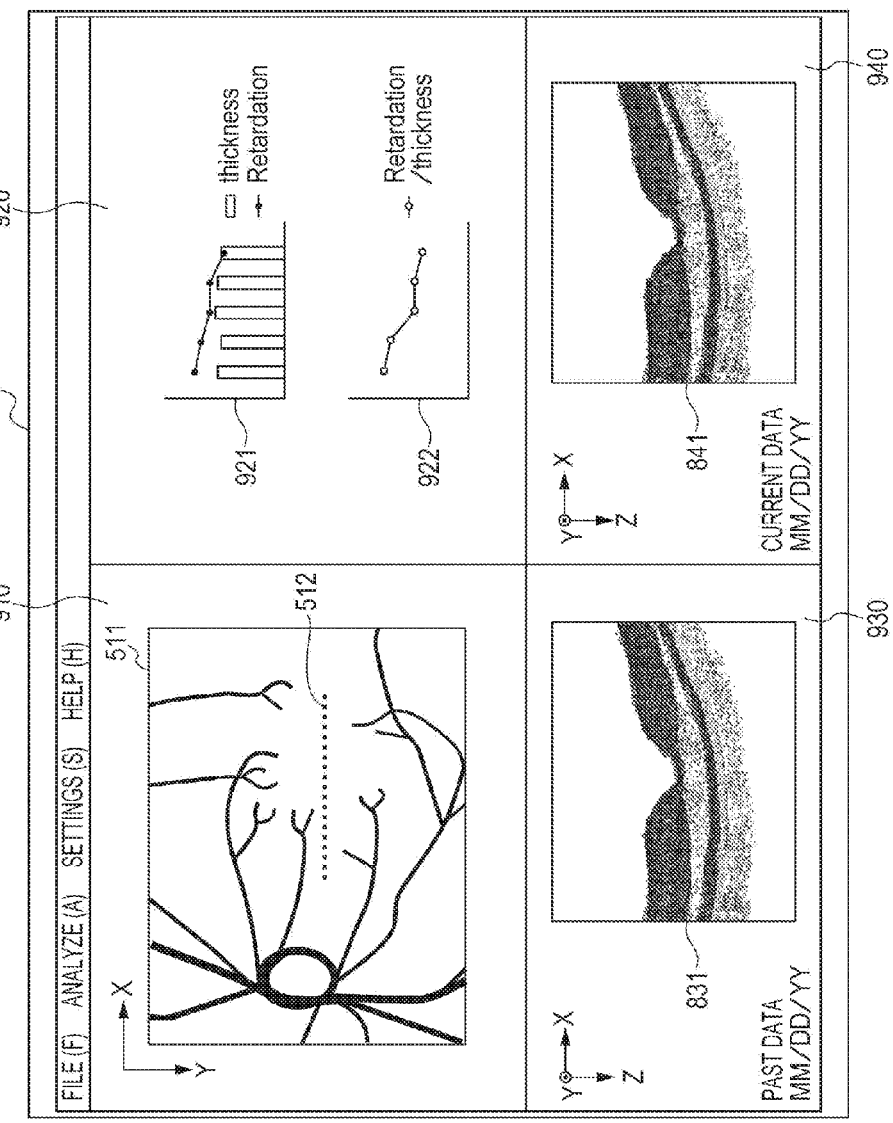
FIG. 9 is a display example of a display screen on the display unit of the image processing apparatus according to the first embodiment.

Note that a graph showing comparison information of a selected region may be displayed instead of the retardation difference image 820. FIG. 9 illustrates an example where, with regard to the RNFL thickness and retardation obtained in step S108, a graph 921 indicating comparison with a value acquired in the past, and a graph 922 indicating comparison with past acquisition values relating to retardation values per thickness, obtained by dividing the retardation by the thickness, as displayed. The horizontal axes of the graphs represent the date, the acquired data being arrayed in time sequence along the horizontal axes. In a case where the number of pieces of acquired data is great, due to follow-up being carried out over a long time, optional past acquisition data can be selected from the comparing unit 196 and displayed on the graph.

The display region 830 which is an example of a third display region displays a past tomographic image 831. The past tomographic image 831 is deformed so as to display the same region as a tomographic image 841. Segmentation may be superimposed in addition to the retardation image at this time, to clarify each layer.

The display region 840 which is an example of a fourth display region displays the currently acquired tomographic image 841. The tomographic image 841 is deformed by performing enlarging rotation, extraction, and so forth of the image (examples of positioning) so that the correlation (value of correlation function) as to the past tomographic image 831 is greater than a threshold value. Segmentation may be superimposed in addition to the retardation image at this time, to clarify each layer.

Note that the display control unit 191 may display a retardation map on any of the display region on the display unit 192 instead of the above-described retardation tomographic images. Alternatively, the display control unit 191 may display a retardation map overlaid on the fundus luminance image 511.

Second Embodiment

A second embodiment will be described with reference to FIGS. 10 and 11. In the present embodiment, a method in which a three-dimensional (3D) image is generated of OCT tomographic images, and tomographic images having high similarity as to OCT tomographic images used in diagnosis in the past are extracted from the currently acquired 3D image data and compared, will be described.

Figure 10:
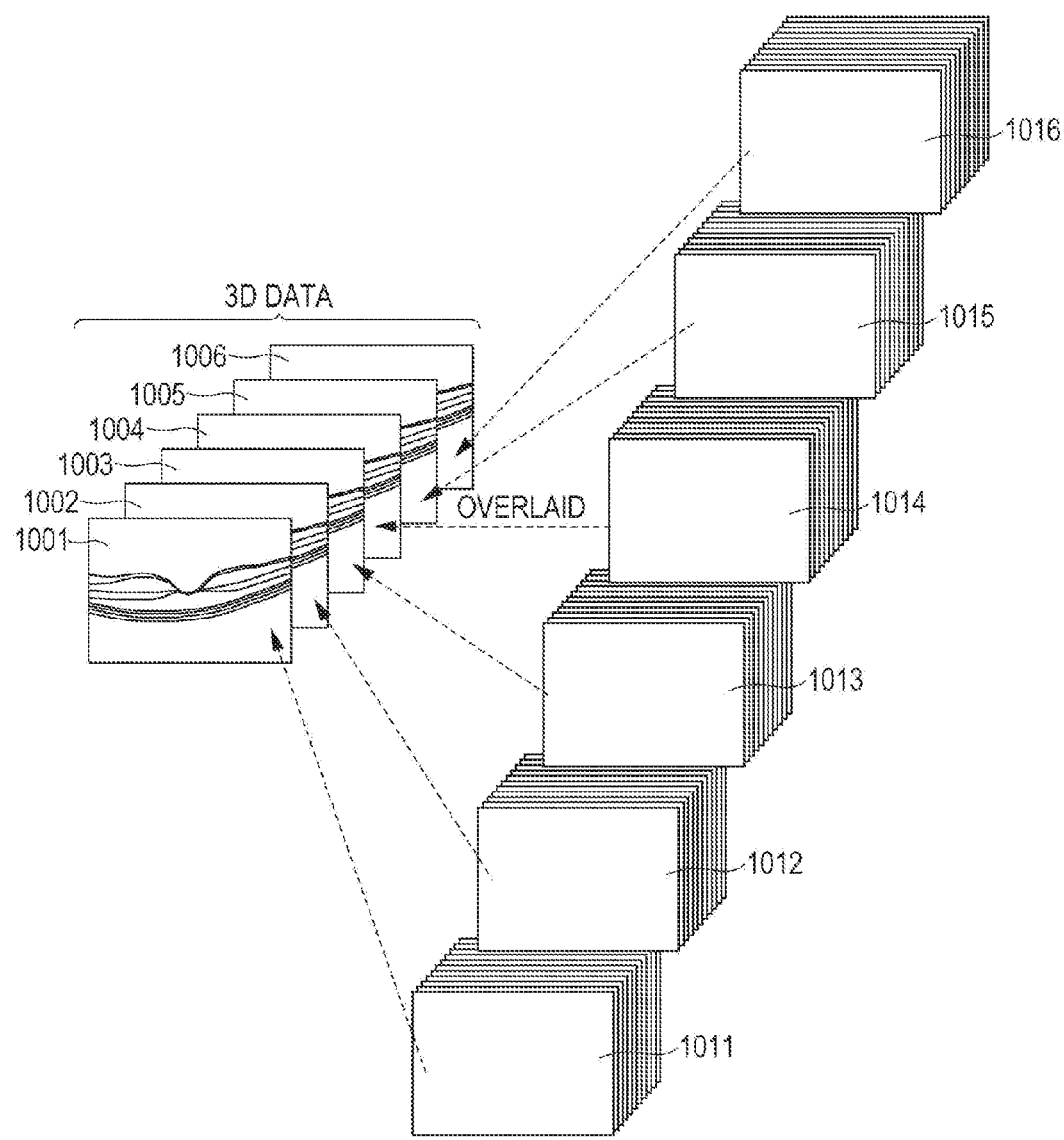
FIG. 10 is a conceptual diagram of a 3D tomographic luminance image, constructed of overlaid images according to a second embodiment.
Figure 11:
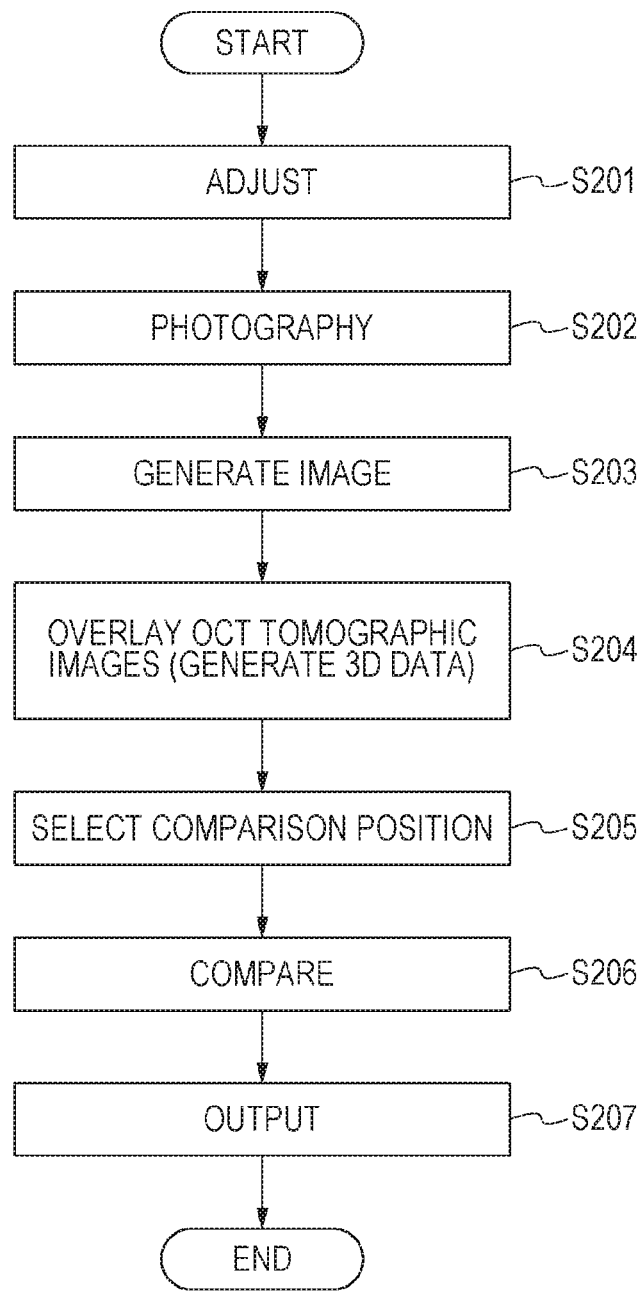
FIG. 11 is a flowchart illustrating processing according to the second embodiment.

As illustrated in FIG. 10, B-scan images making up a 3D image are overlaid to configure the 3D image. For example, a tomographic luminance image 1001 is generated by overlaying a tomographic luminance image group 1011 of N tomographic luminance images acquired at the same scan position. In the same way, tomographic luminance images 1002 through 1006 are generated by overlaying tomographic luminance image groups 1012 through 1016 of N corresponding tomographic luminance images. Thus, a 3D image configured of overlaid B-scan images is created.

Processing Operations

Next, feature processing operations of the present embodiment will be described with reference to the flowchart in FIG. 11. Description of processing operations which are the same as those in the first embodiment will be omitted here.

In the photography in step S202, the driving control unit 180 controls the driving angles of the Y-scanner 107 and Y-scanner 110, and takes N B-scan images while acquiring 3D image data. For example, the Y-scanner 110 is fixed and the X-scanner 107 is scanned N times, thereby acquiring N tomographic luminance images at the same region, following which the Y-scanner 110 is controlled by the driving control unit 180 so as to feed the scan position by one step. The v-scanner 110 scans the set range, thereby acquiring 3D image data having N B-scan images each.

Next, in step S204, the image overlaying unit 195 overlays the corresponding N−1 B-scan images on the B-scan image, thereby generating a 3D image configured of overlaid images, and the comparing unit 196 stores the generated 3D image data.

In step S205, a comparison position between a past tomographic luminance image and current tomographic luminance images is specified, based on the 3D image data configured in step S204. That is to say, in step S205 the overlay-processed current tomographic luminance images are compared with a past tomographic luminance image, and a current tomographic luminance image of which the similarity is the greatest is extracted from the 3D image. Calculation of similarity is performed by correlation function, for example. The image data regarding which similarity is to be compared is already subjected to overlaying processing, so extraction of comparison positions can be performed more accurately.

As described above, extracting luminance images of the same object tissue of an object and evaluating change over time by difference in retardation enables useful information to be provided for physicians diagnosing diseases. For example, in a case where the eye of the patient has glaucoma, luminance images taken periodically over time to follow up on diagnosis and treatment do not change very much, but birefringence may change. This nature is used to perform positioning among luminesce images which do not change much over time, thereby evaluating the difference in retardation of the same object tissue, while avoiding the risk, of positioning shifting during follow up. Accordingly, advance of disease in the same tissue, regarding which change is not readily manifested in luminance images, can be visualized.

Further, periodically acquiring RNFL thickness and retardation for follow-up can provide useful information for diagnosis. For example, in a case where the retinal nerve fiber density of the object has fallen, the birefringence falls, so even if the RNFL thickness is the same, data of the retardation falling can be obtained, which can contribute to early discovery of glaucoma.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment (s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-159177, filed Jul. 31, 2013, which is hereby incorporated by reference herein in its entirety.

The invention claimed is:

1. An image processing apparatus, comprising:
a tomographic image acquiring unit, configured to acquire a plurality of tomographic luminance images obtained by photographing an object at different times, and a plurality of polarization-sensitive tomographic images corresponding to the plurality of tomographic luminance images;
a positioning unit configured to position the acquired plurality of polarization-sensitive tomographic images, by at least deforming at least one of the acquired plurality of polarization-sensitive tomographic images so that correlation of the acquired plurality of tomographic luminance images is greater than a threshold value; and
a generating unit configured to generate a new polarization-sensitive tomographic image, using the plurality of polarization-sensitive tomographic images which are positioned.

2. The image processing apparatus according to claim 1, wherein the tomographic image acquiring unit acquires, as the plurality of polarization-sensitive tomographic images, a past polarization-sensitive tomographic image and a current polarization-sensitive tomographic image,
and wherein the generating unit generates, as the new polarization-sensitive tomographic image, information indicating the difference between the past polarization-sensitive tomographic image and the current polarization-sensitive tomographic image, that have been positioned.

3. The image processing apparatus according to claim 1, wherein the generating unit generates, as the new polarization-sensitive tomographic image, an overlaid image where the plurality of polarization-sensitive tomographic images that have been positioned are overlaid.

4. The image processing apparatus according to claim 3, wherein the generating unit generates, as the overlaid image, a past polarization-sensitive tomographic image and a current polarization-sensitive tomographic image,
wherein the positioning unit positions the generated past polarization-sensitive tomographic image and the generated current polarization-sensitive tomographic image, using information about a past tomographic luminance image corresponding to the generated past polarization-sensitive tomographic image and a current tomographic luminance image corresponding to the generated current polarization-sensitive tomographic image,
and wherein the generating unit generates information indicating the difference between the past polarization-sensitive tomographic image and the current polarization-sensitive tomographic image that have been positioned.

5. The image processing apparatus according to claim 3, wherein the positioning unit positions the acquired plurality of polarization-sensitive tomographic images, by deforming at least one of the acquired plurality of polarization-sensitive tomographic images in accordance with deforming at least one of the acquired plurality of tomographic luminance images so that correlation of the acquired plurality of tomographic luminance images is greater than a threshold value.

6. The image processing apparatus according to claim 3, further comprising a determining unit configured to determine positional shift between the acquired plurality of tomographic luminance images,
wherein the positioning unit positions the acquired plurality of polarization-sensitive tomographic images by the determined positional shift and the deforming.

7. An image processing method, comprising:
a step to acquire a plurality of tomographic luminance images obtained by photographing an object at different times, and a plurality of polarization-sensitive tomographic images corresponding to the plurality of tomographic luminance images;
a step to position the acquired plurality of polarization-sensitive tomographic images, by at least deforming at least one of the acquired plurality of polarization-sensitive tomographic images so that correlation of the acquired plurality of tomographic luminance images is greater than a threshold value; and
a step to generate a new polarization-sensitive tomographic image, using the plurality of polarization-sensitive tomographic images which are positioned.

8. The image processing method according to claim 7, wherein a past polarization-sensitive tomographic image and a current polarization-sensitive tomographic image are acquired as the plurality of polarization-sensitive tomographic images,
and wherein information indicating the difference between the past polarization-sensitive tomographic image and the current polarization-sensitive tomographic image, that have been positioned, is generated as the new polarization-sensitive tomographic image.

9. The image processing method according to claim 7, wherein an overlaid image, where the plurality of polarization-sensitive tomographic images that have been positioned are overlaid, is generated as the new polarization-sensitive tomographic image.

10. The image processing method according to claim 9, wherein a past polarization-sensitive tomographic image and a current polarization-sensitive tomographic image are generated as the overlaid image, wherein the generated past polarization-sensitive tomographic image and the generated current polarization-sensitive tomographic image are positioned, using information about a past tomographic luminance image corresponding to the generated past polarization-sensitive tomographic image and a current tomographic luminance image corresponding to the generated current polarization-sensitive tomographic image, and wherein information, indicating the difference between the past polarization-sensitive tomographic image and the current polarization-sensitive tomographic image that have been positioned, is generated.

11. A non-transitory computer-readable storage medium storing a program for causing a computer to execute an image processing method, the image processing method comprising:
- a step to acquire a plurality of tomographic luminance images obtained by photographing an object at different times, and a plurality of polarization-sensitive tomographic images corresponding to the plurality of tomographic luminance images;
- a step to position the acquired plurality of polarization-sensitive tomographic images, by at least deforming at least one of the acquired plurality of polarization-sensitive tomographic images so that correlation of the acquired plurality of tomographic luminance images is greater than a threshold value; and
- a step to generate a new polarization-sensitive tomographic image, using the plurality of polarization-sensitive tomographic images which are positioned.

12. An image processing apparatus, comprising:
- a tomographic image acquiring unit, configured to acquire a plurality of tomographic luminance images obtained by photographing an object at different times, and a plurality of polarization-sensitive tomographic images corresponding to the plurality of tomographic luminance images;
- a determining unit configured to determine positional shift between the acquired plurality of tomographic luminance images; and
- a positioning unit configured to position the acquired plurality of polarization-sensitive tomographic images based on the determined positional shift.

13. The image processing apparatus according to claim 12, further comprising a comparing unit configured to compare the plurality of polarization-sensitive tomographic images which are positioned.

14. The image processing apparatus according to claim 13, wherein the comparing unit generates information indicating difference between the plurality of polarization-sensitive tomographic images which are positioned by comparing the plurality of polarization-sensitive tomographic images which are positioned.

15. The image processing apparatus according to claim 14, wherein the comparing unit generates a difference image of the plurality of polarization-sensitive tomographic images which are positioned, as the information indicating difference, by comparing the plurality of polarization-sensitive tomographic images which are positioned.

16. The image processing apparatus according to claim 14, further comprising:
- a display control unit configured to display the generated information indicating difference on a display unit.

17. The image processing apparatus according to claim 12, wherein the positioning unit positions the acquired plurality of polarization-sensitive tomographic images so that positional shift between the acquired plurality of polarization-sensitive tomographic images reduces based on the determined positional shift.

18. An image processing method, comprising:
- a step to acquire a plurality of tomographic luminance images obtained by photographing an object at different times, and a plurality of polarization-sensitive tomographic images corresponding to the plurality of tomographic luminance images;
- a step to determine positional shift between the acquired plurality of tomographic luminance images; and
- a step to position the acquired plurality of polarization-sensitive tomographic images based on the determined positional shift.

19. A non-transitory computer-readable storage medium storing a program for causing a computer to execute the steps of the image processing apparatus method to claim 18.

* * * * *